(12) United States Patent
Wang et al.

(10) Patent No.: US 8,337,968 B2
(45) Date of Patent: Dec. 25, 2012

(54) RADIATION STERILIZED MEDICAL DEVICES COMPRISING RADIATION SENSITIVE POLYMERS

(75) Inventors: Lixiao Wang, Long Lake, MN (US); John Jianhua Chen, Plymouth, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1263 days.

(21) Appl. No.: 10/241,278

(22) Filed: Sep. 11, 2002

(65) Prior Publication Data

US 2004/0048016 A1    Mar. 11, 2004

(51) Int. Cl.
*B32B 23/00*  (2006.01)
*B32B 1/02*   (2006.01)

(52) U.S. Cl. .............. 428/35.2; 428/34.1; 428/35.7; 428/35.9; 428/36.9

(58) Field of Classification Search ............... 428/34.1, 428/34.2, 35.7, 35.9, 36.9, 36.92, 35.2, 36.91; 604/264, 96, 915, 916
See application file for complete search history.

(56) References Cited

U.S. PATENT DOCUMENTS

| | | | | |
|---|---|---|---|---|
| 2,856,932 A * | 10/1958 | Griffitts | | 604/171 |
| 3,957,919 A * | 5/1976 | Von Bodungen et al. | | 524/504 |
| 4,139,665 A * | 2/1979 | Herrero | | 428/36.7 |
| 4,490,421 A | 12/1984 | Levy | | 428/35 |
| 4,666,959 A * | 5/1987 | Weissberger et al. | | 523/137 |
| 4,778,656 A * | 10/1988 | Allen et al. | | 422/20 |
| 4,950,239 A | 8/1990 | Gahara | | 604/96 |
| 4,963,313 A | 10/1990 | Noddin et al. | | 264/573 |
| 5,021,515 A | 6/1991 | Cochran et al. | | 525/371 |
| 5,034,252 A | 7/1991 | Nilsson et al. | | 428/35.8 |
| 5,051,490 A | 9/1991 | Joyce et al. | | 528/190 |
| 5,108,412 A | 4/1992 | Krumeich et al. | | 606/166 |
| 5,137,688 A * | 8/1992 | DeRudder | | 422/22 |
| 5,264,260 A | 11/1993 | Saab | | 428/35.5 |
| 5,328,468 A | 7/1994 | Kaneko et al. | | 604/96 |
| 5,348,538 A | 9/1994 | Wang et al. | | 604/96 |
| 5,433,713 A | 7/1995 | Trotta | | 604/264 |
| 5,500,180 A | 3/1996 | Anderson et al. | | 264/532 |
| 5,531,719 A | 7/1996 | Takahashi | | 604/280 |
| 5,554,120 A | 9/1996 | Chen et al. | | 604/96 |
| 5,556,383 A | 9/1996 | Wang et al. | | 181/282 |
| 5,559,167 A * | 9/1996 | Mahood | | 523/136 |
| 5,599,863 A * | 2/1997 | Zimmerman | | 524/308 |
| 5,744,056 A | 4/1998 | Venkateshwaran et al. | | 252/188.28 |
| 5,797,877 A | 8/1998 | Hamilton et al. | | 604/96 |
| 5,830,182 A * | 11/1998 | Wang et al. | | 604/96.01 |
| 5,951,941 A | 9/1999 | Wang et al. | | 264/523 |
| 6,017,859 A * | 1/2000 | Rossi et al. | | 508/591 |
| 6,033,778 A | 3/2000 | Kakihara et al. | | 428/364 |
| 6,048,299 A * | 4/2000 | Hoffmann | | 600/3 |
| 6,093,463 A | 7/2000 | Thakrar | | 428/36.9 |
| 6,139,935 A | 10/2000 | Cullen et al. | | 428/68 |
| 6,239,276 B1 * | 5/2001 | Gupta et al. | | 544/213 |
| 6,383,585 B2 | 5/2002 | Peiffer et al. | | 428/35.9 |
| 6,428,882 B1 | 8/2002 | Peiffer et al. | | 428/220 |
| 6,479,160 B1 * | 11/2002 | Tsai et al. | | 428/474.4 |

FOREIGN PATENT DOCUMENTS

| | | |
|---|---|---|
| EP | 0 401 772 | 12/1990 |
| EP | 0 537 069 A1 | 4/1993 |
| EP | 0 697 219 A2 | 2/1996 |
| WO | 86/01813 A1 | 3/1986 |
| WO | 96/18686 | 6/1996 |
| WO | 96/37240 A1 | 11/1996 |
| WO | 98/13266 | 4/1998 |
| WO | 99/13924 A2 | 3/1999 |
| WO | 99/38914 | 8/1999 |
| WO | 01/39810 A1 | 6/2001 |

OTHER PUBLICATIONS

Malcolm P. Stevens, Polymer Chemistry: An Introduction, Second Edition, pp. 7-8 (1990).*
Patent Abstracts of Japan 56-060642 (May 1981).

* cited by examiner

*Primary Examiner* — Marc Patterson
(74) *Attorney, Agent, or Firm* — Vidas, Arrett & Steinkraus, P.A.

(57) ABSTRACT

A medical device, for instance a device inserted into the body such as catheter or a balloon, at least a portion of which is made of a thermoplastic polymeric material. The thermoplastic polymeric material comprises a blend or laminate of an aromatic protectant polymer and a radiation sensitive polymer, and/or the polymeric material includes a stabilizer against radiation oxidative degradation. The device is sterilized by exposure to high energy radiation.

25 Claims, No Drawings

RADIATION STERILIZED MEDICAL DEVICES COMPRISING RADIATION SENSITIVE POLYMERS

FIELD OF THE INVENTION

The present invention relates to the field of medical devices made from thermoplastic polymers, especially devices inserted into the body, for instance tubular devices such as catheters and high strength balloons used thereon, and to polymer compositions used to prepare such devices.

BACKGROUND OF THE INVENTION

A wide variety of medical devices are made from thermoplastic polymers. Medical devices must be manufactured with greater care than general consumer products especially when inserted into the body or brought into contact with a wound or lesion. In the area of treatment devices, such as catheters, manufacturers must take great care to assure that the devices perform with an extremely high degree of reliability. At the same time there is a need to develop materials and improve processing techniques to obtain improvements in desirable properties such as tensile strength, flexibility, puncture resistance, and softness. One area in which development has been especially intense focuses on balloons deployed on catheters which are utilized for dilatation, especially angioplasty, for stent placement, for urinary treatment, and the like.

In preparing high strength balloons for medical devices such as dilatation and stent placement catheters, a variety of polymer materials have been used.

Levy, U.S. Pat. No. 4,490,421, describes use of PET of high molecular weight (1.0 IV or higher). The patent notes that the IV may decrease during processing into balloons. Such a decrease is believed to be related to polymer degradation caused by extrusion temperature and the time the resin is held in the melt. Lower molecular weight PET has also proven useful for preparing high strength balloons. See for instance Noddin et al, U.S. Pat. No. 4,963,313; Saab, U.S. Pat. No. 5,264,260; Wang et al U.S. Pat. No. 5,348,538. PET is a polyester derived from an aromatic diacid and an aliphatic diol.

Aliphatic polyamide balloons are described in Pinchuk, U.S. Pat. No. 5,108,412.

Polyurethane block copolymer balloons are described in Gahara, U.S. Pat. No. 4,950,239, and Anderson et al, U.S. Pat. No. 5,500,180. The polyurethane polymers may be derived from aromatic polyisocyanates.

Polyamide block copolymer balloons and polyester block copolymer balloons are described in Wang et al, U.S. Pat. No. 5,563,383. The polyamide block copolymers are entirely aliphatic, whereas the polyester block copolymers comprise aromatic poloyester segments and aliphatic polyether segments.

Various other polymers have also been used for catheter balloons.

A wide variety of polymer blends have also been described for such balloons, for instance, Sahatjian et al, U.S. Pat. No. 5,500,180; Chen et al, U.S. Pat. No. 5,554,120, Hamilton et al, U.S. Pat. No. 5,797,877. Some such blends have included compatibility enhancing additives. However, heretofore it has not been proposed to include additives which maintain or increase molecular weight during melt processing.

U.S. Pat. No. 5,328,468 describes balloons for a vascular dilatation catheter which is formed from an aromatic polyamide or alloy thereof.

U.S. Pat. No. 5,951,941 describes catheter balloons made from a block copolymer thermoplastic elastomer which may be a polyamide/polyether/polyester. The polyamide segments optionally may be aromatic polyamide segments.

U.S. Pat. No. 5,531,719 describes a catheter tube structure in which a proximal portion of the tube has an inner tube bonded to an outer tube. The inner tube maybe formed of a variety of materials including a polyamide elastomer block copolymer in which the polyamide blocks are optionally aromatic polyamide.

U.S. Pat. No. 6,033,778 describes an aromatic polyamide bristle said to be useful for tension member, fishing line and catheter.

Balloon catheters and other medical devices made from polymeric materials are most conventionally sterilized by exposure to a sterilizing gas such as ethylene oxide. High energy radiation (e-beam, x-ray and/or γ-ray radiation) has been used for sterilization of devices made from some polymers but is not widely suitable for devices made from thermoplastic polymers because it degrades many such polymers by inducing polymer scission, crosslinking and/or oxidization reactions. Aliphatic polymers are particularly susceptible to degradation from high energy radiation. Aromatic polymers have been observed to have resistance to high energy radiation.

SUMMARY OF THE INVENTION

The invention pertains to medical devices formed from thermoplastic polymer material, particularly devices inserted into the body such as catheters and catheter balloons, at least a portion of which is made of a thermoplastic polymer material.

In one aspect the invention is a sterile medical device formed from thermoplastic polymer material wherein:
a) the thermoplastic polymer material comprises a radiation sensitive polymer characterized by an aromatic content of from 0 to about 20% by weight and an aromatic protectant polymer having an aromatic content of at least 5% by weight greater than the aromatic content of the radiation sensitive polymer, and
  i) the thermoplastic polymer material is a melt blend mixture comprising said radiation sensitive polymer and said aromatic protectant polymer, and/or
  ii) the thermoplastic polymer material comprises a multilayer laminate, at least one layer comprising said radiation sensitive polymer and at least one layer comprising said aromatic protectant polymer, and
b) the medical device has been sterilized with high energy radiation.

The blends and laminates of the invention permit fashioning of devices which take advantage of high energy radiation stability of the aromatic polymer and of other desirable properties of polymers which have little or no aromatic content. Consequently, high energy radiation sterilization can be practiced with a wider range of devices than has heretofore been available.

In another aspect the invention is a sterile medical device formed from thermoplastic polymer material wherein:
  the thermoplastic polymer material includes a stabilizer against radiation oxidative degradation, and
  the medical device has been sterilized with high energy radiation.

In a further aspect, the invention is a process for preparing a medical device comprising forming at least a part of the device from a polymeric material and subsequently sterilizing the device, wherein a) the device is sterilized by exposure to high energy radiation and
b) (i) the polymeric material comprises a blend of an aromatic protectant polymer and a radiation sensitive polymer,
  ii) the thermoplastic polymer material is a multilayer laminate, at least one layer comprising said radiation sensitive polymer and at least one layer comprising said aromatic protectant polymer, and/or
  (iii) the polymeric material includes a stabilizer against radiation Other aspects of the invention are set forth in the detailed description and claims provided below.

DETAILED DESCRIPTION

All published documents, including all US patent documents, mentioned anywhere in this application are hereby expressly incorporated herein by reference in their entirety. Any copending patent applications, mentioned anywhere in this application are also hereby expressly incorporated herein by reference in their entirety.

The radiation sensitive polymer utilized in some aspects of the invention is suitably one which provides desirable properties to the medical device, such as flexibility, softness, resilience, etc, which are not readily available in aromatic polymers. Exemplary radiation sensitive polymers include thermoplastic resins such as aliphatic polyamides; aliphatic polyamide block copolymers, for instance copolymers formed of aliphatic polyamide blocks and aliphatic polyether or polyester blocks; modified polyolefins, butyl rubbers, aliphatic polyesters, aliphatic polyurethanes. Mixtures of such polymers may be used. The radiation sensitive polymer may be a copolymer containing some aromatic monomer. For purposes of the present invention a polymer having not more than 20%, aromatic content (taken as weight fraction of aromatic groups divided by total weight of polymer) may be a radiation sensitive polymer.

Illustrative aliphatic polyamides include nylon 6, nylon 64, nylon 66, nylon 610, nylon 610, nylon 612, nylon 46, nylon 9, nylon 10, nylon 11, nylon 12, and mixtures thereof. Illustrative aliphatic polyamide block copolymers are polyamide elastomers including the polyamide-polyether-polyesters sold under the PEBAX trademark by AtoChem. especially PEBAX polymers of hardness grades 35-72, and more especially 65-72, for instance PEBAX 6333, 7033 and 7233. Illustrative aliphatic polyurethanes include TECOPHILIC resins available from Thermedics, Inc. Illustrative modified olefins include ENGAGE polymers and SURYLN ionomer modified polyolefins sold by DuPont Dow Elastomers, and EXACT polymers available from Exxon Chemical.

In one aspect of the invention the radiation sterilized device comprises a blend of the radiation sensitive polymer and a aromatic protectant polymer. An aromatic protectant polymer, as used herein, is a polymer having aromatic groups on at least a portion of the repeat units thereof in an amount to provide the polymer with an aromatic content at least 5% by weight greater than the radiation sensitive polymer. The aromatic group containing repeat units ("aromatic repeat units") may be randomly or regularly interspersed with repeat units having no aromatic groups. Desirably the aromatic polymer will have an aromatic content of at least 5%, more particularly about 10% to about 80% by weight, and especially about 20% to about 55% by weight. For purposes of this calculation, only aromatic ring atoms (carbon or hetero atoms of the ring) are considered in calculating aromatic weight. The balance is considered non-aromatic. Specific examples of aromatic protectant polymers include aromatic polyesters, polyphenylene oxides, random or block copolymers of aromatic polyesters, aromatic polyurethanes, aromatic polyureas, aromatic polyamides, block copolymers of aromatic polyamides, styrenic polymers and copolymers, and mixtures of any of the above. Aromatic polyesters include esters of aromatic dicarboxylic acids and copolymers thereof, esters of aromatic diols and copolymers thereof, and polymers comprising both residues of aromatic diacids and residues of aromatic diols. Oxygen scavenging aromatic polyesters such as disclosed in WO 98/13266, incorporated herein by reference, are further examples of suitable aromatic protectant polymers.

In particular examples of this aspect of the invention the aromatic protectant polymer is an aromatic polyamide, polyester or polyurethane. The term aromatic polyamide used herein designates a polyamide which may be considered to be the polymeric product obtained by polycondensing a diamine and a dicarboxylic acid, at least a part of the diamine and/or the dicarboxylic acid containing an aromatic ring. The term aromatic polyester designates a polyester which may be considered to be the polymeric product obtained by polycondensing a diol and a dicarboxylic acid, at least a part of the diol and/or the dicarboxylic acid containing an aromatic ring. The term aromatic polyurethane similarly designates a polyurethane which may be considered to be the polymeric product obtained by polycondensing a diol and a diisocyanate, at least a part of the diol and/or the diisocyanate containing an aromatic ring. It should be noted, that these descriptions are of the final repeat structure not the process of preparation, which may in fact have utilized different starting components and/or a different process sequence. That is, the polymers "may be considered to be" such a designated polycondensation product if its overall repeat unit structure is substantially what would be expected from the respective diamine/diacid, diol/diacid or diol/diisocyanate reaction. In comparing such products any chiral differences or molecular weight sizes should not be taken as substantial differences.

The diamine, diol, dicarboxylic acid and/or diisocyanate moieties containing an aromatic ring may suitably constitute from 20 to 100% by weight, and more suitably from 40 to 60% by weight of the aromatic protectant polymer. It is to be noted that the molar ratio of the diamine, diol, dicarboxylic acid and diisocyanate moieties containing an aromatic ring, to any diamine, diol or dicarboxylic acid moieties containing no aromatic ring, is not necessarily 1:1. It is also to be noted that the aromatic polyamides, polyesters, or polyurethanes may be copolymers including one or more different aromatic moieties and one or more different non-aromatic moieties.

Typical diamines, diols, dicarboxylic acids and diisocyanates having at least one aromatic ring include those represented by general formulae:

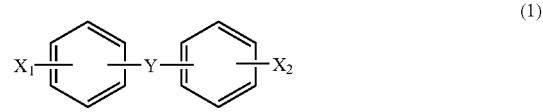

(1)

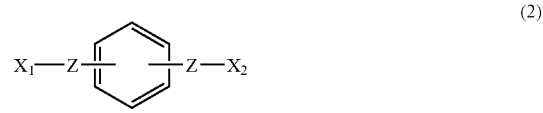

(2)

(3)

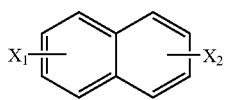

(4)

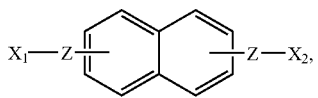

(5)

wherein

X$_1$ and X$_2$ independently represent —COOH, OH, NCO or —NH$_2$;

Y is a divalent group selected from —O—, —S—, —SO$_2$—, —(CH$_2$)$_n$— wherein n is 1 to 4, —CH(CH$_3$)CH$_2$—, —O(CH$_2$)$_n$O— wherein n is 0 to 4, —COO—, —CONH—, and —C(CH$_3$)$_2$—;

Z is a divalent group selected from —O(CH$_2$)$_n$ wherein n is 1 to 4, and —(CH$_2$)$_n$— wherein n is 1 to 4;

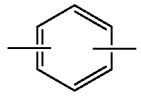

is a benzene ring which may be substituted at any position; and

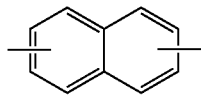

is a naphthalene ring which may be substituted at any position.

The diamines, diols, dicarboxylic acids and diisocyanates having at least one aromatic ring may also be entities which provide aromatic groups pendant to the polymer chain.

Typical aliphatic diamines, diols, dicarboxylic acids or diisocyanates having no aromatic ring therein include diamines, diols and dicarboxylic acids derived from a straight-chain, a branched, or an alicyclic hydrocarbon, as represented by general formulae (6-10) wherein X$_1$ and X$_2$ are as previously defined:

X$_1$—(CH$_2$)$_n$—X$_2$, wherein n is 2 to 12 (6),

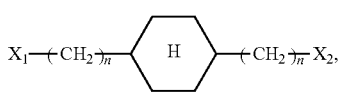

(7)

X$_1$—((C$_p$H$_{2p}$O)$_m$ C$_q$H$_{2q}$)—X$_2$, where m is 1 to 1,000 and p and q are integers of 1-4 (8), a dimer acid (9), and, X$_1$—(CH$_2$C(CH$_3$)$_2$CH$_2$)$_m$—X$_2$, wherein m is 1 to 4 (10).

The aromatic protectant polymer may have a polymerization degree of approximately 50 to 2,000,000, suitably approximately 500 to 500,000, and especially an average molecular weight of approximately 3,000 to 200,000.

Examples of the aromatic polyamides mentioned above, include nylon MXD6 synthesized from m-xylylenediamine and adipic acid and nylon 6I synthesized from hexamethylene-diamine and isophthalic acid. Examples of aromatic polyesters include polyethylene terephthalate, polybutylene terephthalate, polyethylene naphthalate, polyethylene isophthalate, polybutylene isophthalate, and succinate, glutarate, adipate and/or diphenate polyesters of one or more of hydroquinone, resorcinol, distyrene glycol, bisphenol A, diglycidyl ether of bisphenol A, styrene oxide, 1,2-dihydroxynaphthalene, and/or 1,6-dihydroxynaphthalene, and the like. Examples of aromatic polyurethanes include polyether based aromatic polyurethanes such as TECOTHANE resins available from Thermedics, for instance Tecothane 1065D and 1075D, PELLETHANE 2363 available from Dow Plastics, and BIONATE polymers available from Polymer Technology Group, especially 65D grades and higher. Styrenic polymers and copolymers, such as ABS and polystyrene, may also be used as aromatic protectant polymers.

The aromatic protectant polymer as described above may be used in a polymer blend with the radiation sensitive polymer. Desirably the aromatic protectant polymer is present in the blend in an amount of from about 5 to about 95% by weight of the blend, with the balance being a radiation sensitive blend, suitably 10% to 90%, especially 20% to 80%. Desirably the aromatic protectant polymer has a sufficient aromatic content to provide the total blend with an aromatic content of at least 4% by weight thereof, suitably 5 to 65%, especially 10 to 50% by weight.

In one embodiment the aromatic protectant polymer is an aromatic polyamide and the radiation sensitive polymer is an aliphatic polyamide, a non-aromatic polyamide elastomer or a mixture thereof.

The following are examples of partial aromatic polyamide resins which are useful in the invention as aromatic protectant polymers for preparing E-beam resistant medical devices (particularly catheter shafts and balloons): Trogamid T 5000 from Huls AG; Grivory G21 PPA, PA6I/6T, film grade (balloon grade) from EMS-Chemie AG; Grilamid TR partial aromatic, transparent PA12 from EMS-Chemie A; Grivory GV partial aromatic (PA+PPA), semi crystalline Tm=260° C. from EMS-Chemie AG; Grivory HT1 (320° C.) and Grivory HT2(310° C.) PPA (polyphthalamide, semicrystalline) from EMS-Chemie AG; Grivory GTR45 PPA(polyphthalamide, transparent) from EMS-Chemie; Cristamid MS 1100 and Cristamid MS 1700 from ATOFINA; and Nylon MXD6 6121, a condensation product of m-xylylenediamine and adipic acid from Mitsubushi Gas Chemical Company, Inc. These aromatic protectant polymers may be blended with an aliphatic polyamide or polyamide elastomer. In particular: nylon 11; nylon 12; nylon 610; Nylon 612 and polyamide elastomers such as PEBAX 7033 and 7233. Examples of blends include Nylon 12 or Pebax 7233, as the radiation sensitive polymer, and Nylon MXD6, Cristamid MS 1100, Grivory G21 or Trogamid T5000, as the aromatic protectant polymer, in weight ratios of 5/95, 10/90, 20/80, 30/70, 40/60, 50/50, 60/40, 70/30, 80/20, 90/10 and 95/05.

As an alternative to blending, the aromatic protectant polymer and the radiation sensitive polymer may be fashioned into a laminate structures of 2-20 alternating layers of each polymer, for instance by multilayer coextrusion techniques. An oxygen barrier polymer may be employed as aromatic protectant polymer or provided in a separate layer under the aromatic protectant layer. Examples of oxygen barrier polymers which may also function as aromatic protectant include: ethylene terephthalate/naphthalate copolymers, such as described in U.S. Pat. No. 6,428,882 and U.S. Pat. No. 6,383,585; poly[hexamethyleneisophthalamide/terephthalamide] copolymers such as SELAR® PA 3426; aromatic thermoplastic polyarylates containing structural units derived from a bisphenol of cyclohexanone, preferably 1,1-bis(4-hydroxy-3-methylphenyl)cyclohexane, and an aromatic dicarboxylic acid or mixture of such acids, such as described in U.S. Pat. No. 5,051,490. In a multi-layer structure a radiation sensitive polymer layer may be protected from high energy radiation degradation by an outer layer of aromatic protectant polymer and a intermediate layer of an oxygen barrier, which may or may not be an aromatic polymer. Examples of non-aromatic oxygen barrier polymers are polyvinyl alcohol, ethylene-vinyl alcohol copolymers, and nylons 6 and 66.

In other embodiments the aromatic protectant polymer is an aromatic polycarbonate and the radiation sensitive polymer is a polyester-polyether copolymer, such as a HYTREL block copolymer.

Degradation of polymer properties during exposure to sterilizing radiation may also be resisted by including in a polymer composition a stabilizer against radiation oxidative degradation ("ROD" stabilizer). Such ROD stabilizers may be antioxidants, particularly radical or oxygen scavengers. Mercapto compounds, hindered phenols, phosphites, phosphonites and hindered amine antioxidants are among the most effective such stabilizers. Specific examples of stabilizers are 2-mercaptobenzimidazole, trilauryl phosphite, IONOX 330, 2-mercaptobenzothiazole, N,N-di(β-napthyl-p-phenylenediamine((DPPD), SANTONOX R, SANTOWHITE powder, phenothiazine, IONOL, 2,6-di-t-butylcresol, N-cyclohexyl-N'-phenyl-p-phenylenediamine, nickel dibutyldithiocarbamate, IRGANOX 1010, 3-(3,5-di-t-butyl-6-hydroxyphenyl) propionate, 1,2,2,6,6-pentamethyl-4-stearoyl piperidine, and 2,2,6,6, tetramethyl-4-nitropiperidine. Further examples include butylated reaction product of p-cresol and dicyclopentadiene, substituted amine oligomers, N,N'-bis(2,2,6,6-tetramethyl-4-piperidinyl)-1,6-hexanediamine, 2,4-dichloro-6-(4-morpholinyl)-1,3,5-triazine, and N,N'-hexamethylene-bis[3-(3,5-di-t-butyl-4-hydroxyphenyl) propionamide].

Still further, various metals or compounds thereof may function as ROD stabilizers by oxygen scavenging using preferential oxidization of a metal or metal compound, for instance iron, cobalt, nickel, ruthenium, rhodium, palladium, osmium, iridium, platinum, copper, manganese and zinc metal and compounds thereof, as described in JP 56-60642-A (1981); WO 99/38914, U.S. Pat. No. 5,034,252, U.S. Pat. No. 5,021,515, U.S. Pat. No. 5,744,056 and U.S. Pat. No. 6,139,935, all expressly incorporated herein by reference. A suitable approach is to incorporate a mixture of an oxidizable metal (e.g., iron, aluminum, magnesium, titanium, tin or zinc) or oxidizable metal compound (e.g. iron (II) oxide), and one or more electrolyte or other assistant compounds (e.g. a hydroxide, carbonate, sulfite, thiosulfite, tertiary phosphate, secondary phosphate, organic acid salt or halide of an alkali metal or alkaline earth metal) into a suitable resin, melt process the result into monolayer or multilayer sheets, films or tubes and form the resulting oxygen scavenger-containing material into a device. As an example, the metal may be iron. The iron may be either hydrogen reduced iron or electrolytically reduced iron, or chemically reduced iron which will provide greater reactivity. Suitable electrolyte salts are sodium chloride, sodium sulfate, potassium chloride, ammonium chloride, ammonium sulfate, calcium chloride, sodium phosphate, calcium phosphate and magnesium chloride. A solid non-electrolytic acidic compound such as sodium acid pyrophosphate may also be employed in such systems.

The ROD stabilizers may be employed in the polymer compositions in amounts of from about 0.01% to about 5%, suitably from about 0.1 to about 1%, for instance from 0.2% to 0.5%. The stabilizer can be compounded into the polymer composition in the extrusion melt or in a separate compounding step prior thereto.

The ROD stabilizer may also be an oxygen scavenging polymer, such as the polyketone polymers described in WO 96/18686 of the formula

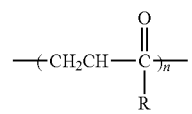

where R is H, an organic side chain or a silicon side chain, and n is a positive number greater than 2. Such polyketone ROD stabilizers are suitably employed in the thermoplastic composition in an amount of from 0.1 to about 10% by weight.

The ROD stabilizers may be added to any in thermoplastic polymer composition utilized in a medical device, especially compositions employing radiation sensitive polymers as described above. In some embodiments the radiation sensitive polymer may be combined with both an aromatic protectant polymer as described above and an ROD stabilizer. The ROD stabilizer is compounded with the polymer in a polymer melt stage. Thermal and/or hydrolytic stabilizers may also be included in the compounding step, especially if the polymer has a poor thermal or hydrolytic stability.

An oxygen scavenger or antioxidant ROD stabilizer, may also be compounded into the polymer material of some or all layers of laminate structures, preferably into at least the outer layer of a laminate. For instance the outer layer of a tube comprising 2-20 alternating layers of two or more of polymer compositions, at least one of which may be radiation sensitive in the absence of the stabilizer. The polymer compositions may be based on the same or different polymers. In structures having an inner layer which is exposed to oxygen penetration, the use of an oxygen scavenger or antioxidant can also be beneficial in reducing radiation damage to central layer(s) by depriving oxygen access to the central layers. Examples of such laminates include catheter shaft or catheter balloon tubing having a core layer of PEBAX 7233 and an outer layer of PEBAX 7033 or PEBAX 7233, which has been compounded with one or more ROD stabilizers; catheter shaft or catheter balloon tubing having a core layer of PEBAX 7233 and both an inner layer and an outer layer of PEBAX 7033, or PEBAX 7233, which has been compounded with one or more ROD stabilizers; 5, 7, 9, 11 or 13-layer catheter shaft or catheter balloon tubing formed of alternating layers of i) PEBAX 7033, or PEBAX 7233, which has been compounded with one or more ROD stabilizers and 2) of PEBAX 7233 which is uncompounded.

Further, an oxygen barrier polymer such as discussed above may be formulated with an ROD stabilizer and used as an outer layer, or as an intermediate layer between an outer radiation protectant layer and a core layer of a radiation sensitive polymer.

High energy radiation which may be used for sterilization includes e-beam, γ-ray and x-ray radiation. Various commercial sterilizations services are available to perform such tasks including Titan Corp. (X-ray and e-beam) and SteriGenics International (γ-ray).

The above examples and disclosure are intended to be illustrative and not exhaustive. These examples and description will suggest many variations and alternatives to one of ordinary skill in this art. All such alternatives and variations are intended to be included within the scope of the claims, where the term "comprising" means "including, but not limited to". Those familiar with the art may recognize other equivalents to the specific embodiments described herein which equivalents are also intended to be encompassed by the claims. For instance, an aromatic protectant polymer and/or a radiation sensitive polymer may be a polymer produced by a polymerization mechanism other than those specifically described above, for instance a radical, anionic or cationic addition polymerization mechanism, without departing from the hereof.

Further, the particular features presented in the dependent claims can be combined with each other in other manners within the scope of the invention such that the invention should be recognized as also specifically directed to other embodiments having any other possible combination of the features of the dependent claims. For instance, for purposes of claim publication, any dependent claim which follows should be taken as alternatively written in a multiple dependent form from all prior claims which possess all antecedents referenced in such dependent claim if such multiple dependent format is an accepted format within the jurisdiction (e.g. each claim depending directly from claim 1 should be alternatively taken as depending from any previous claims).

The invention claimed is:

1. A sterile medical catheter or balloon at least a portion of which is formed from thermoplastic polymer material wherein:
   a) the thermoplastic polymer material comprises at least one radiation sensitive polymer characterized by an aromatic content of from 0 to about 20% by weight which is a member selected from the group consisting of aliphatic polyamides, aliphatic polyamide block copolymers, copolymers formed from aliphatic blocks and aliphatic polyester blocks, ethylene-alpha olefin copolymers, ionomer modified polyolefins, butyl rubbers, aliphatic polyesters, aliphatic polyurethanes and mixtures thereof and an aromatic protectant polymer which protects against degradation caused by exposure to high energy radiation, the aromatic protectant polymer having an aromatic content of at least 5% by weight greater than the aromatic content of the radiation sensitive polymer and which is a member selected from the group consisting polyphenylene oxides, aromatic polyurethanes, aromatic polyureas, aromatic polyamides, block copolymers of aromatic polyamides, and mixtures thereof, and
      i) the thermoplastic polymer material is a melt blend mixture comprising said radiation sensitive polymer and said aromatic protectant polymer, and/or
      ii) the thermoplastic polymer material comprises a multilayer laminate, at least one layer comprising said radiation sensitive polymer and at least one layer comprising said aromatic protectant polymer, and
   b) the catheter or balloon has been sterilized with high energy radiation.

2. A catheter or balloon as in claim 1 wherein the radiation sensitive polymer is free of aromatic groups.

3. A catheter or balloon as in claim 2 wherein the polymeric material is a melt blend mixture and the aromatic content thereof is at least 4% by weight of the blend.

4. A catheter or balloon as in claim 1 wherein the aromatic content of the aromatic protectant polymer is from about 10 to about 80% by weight of the aromatic protectant polymer.

5. A catheter or balloon as in claim 1 wherein the radiation sensitive polymer is a polyamide-polyether-polyester block copolymer.

6. A catheter or balloon as in claim 1 wherein the aromatic protectant polymer is present in said melt blend mixture in an amount of from about 5 to about 95% by weight of the mixture.

7. A catheter or balloon as in claim 6 wherein the aromatic content of said aromatic protectant polymer is at least 20% by weight thereof.

8. A catheter or balloon as in claim 1 wherein the aromatic protectant polymer is an oxygen barrier polymer.

9. A catheter or balloon as in claim 1 wherein the thermoplastic polymer material comprises a multilayer laminate comprising at least one layer of said radiation sensitive polymer and at least one layer of said aromatic protectant polymer.

10. A catheter or balloon as in claim 9 in the form of a tube having a plurality of longitudinally extending layers and said layer of aromatic protectant polymer is an outer layer relative to said layer of radiation sensitive polymer.

11. A catheter or balloon as in claim 10 wherein the aromatic protectant polymer is an oxygen barrier polymer.

12. A catheter or balloon as in claim 10 wherein a layer of an oxygen barrier polymer is located intermediate said aromatic protectant polymer and radiation sensitive polymer layers.

13. The catheter or balloon of claim 1, said thermoplastic polymer material further comprising a stabilizer against radiation oxidative degradation, the medical device has been sterilized with high energy.

14. A catheter or balloon as in claim 13 wherein the stabilizer is present the polymer composition in an amount of from about 0.01% to about 5% by weight.

15. A catheter or balloon as in claim 13 wherein the stabilizer is selected from the group consisting of mercapto compounds, phosphites, phosphonites hindered phenols and hindered amine antioxidants.

16. A catheter or balloon as in claim 14 wherein the thermoplastic polymer material is a multilayer laminate of said radiation sensitive polymer and said aromatic protectant polymer.

17. A catheter or balloon as in claim 14 wherein the stabilizer against radiation oxidative degradation comprises a polyketone of the formula:

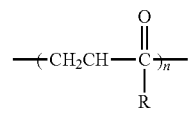

where R is H, an organic side chain or a silicon side chain, and n is a positive number greater than 2.

18. A catheter or balloon as in claim 17 wherein said polyketone is present in the thermoplastic composition in an amount of from 0.1 to about 10% by weight.

19. A sterile medical device at least a portion of which is formed from thermoplastic polymer material wherein:
   a) the thermoplastic polymer material comprises a radiation sensitive polymer characterized by an aromatic content of from 0 to about 20% by weight which is a member selected from the group consisting of aliphatic polyamides, aliphatic polyamide block copolymers, copolymers formed from aliphatic blocks and aliphatic polyether blocks, copolymers formed from aliphatic blocks and aliphatic polyester blocks, ethylene-octene copolymers, ethylene-butene copolymers, ethylene-hexene copolymers, ionomer modified polyolefins, butyl rubbers, aliphatic polyesters, aliphatic polyurethanes and mixtures thereof and an aromatic protectant polymer which protects against degradation caused by exposure to high energy radiation, the aromatic protectant polymer having an aromatic content of at least 5% by weight greater than the aromatic content of the radiation sensitive polymer, and the thermoplastic polymer material comprises a multilayer laminate, at least one layer comprising said radiation sensitive polymer and at least one layer comprising said aromatic protectant polymer,
b) the medical device has been sterilized with high energy radiation and
c) at least a portion of the device is adapted for insertion into the body and said thermoplastic polymer material occurs on said portion.

20. A sterile medical device as in claim 19 wherein the aromatic protectant polymer is selected from the group consisting of aromatic polyesters, block copolymers of aromatic polyesters, aromatic polyurethanes, aromatic polyamides, block copolymers of aromatic polyamides and mixtures thereof.

21. A sterile medical device as in claim 20 further comprising a stabilizer against radiation oxidative degradation wherein the stabilizer is selected from the group consisting of 2-mercaptobenzimidazole, trilauryl phosphite, 2-mercaptobenzothiazole, N,N-di(β-napthyl-p-phenylenediamine, phenothiazine, 2,6-di-t-butylcresol, N-cyclohexyl-N'-phenyl-p-phenylenediamine, nickel dibutyldithiocarbamate, β-(3,5-di-t-butyl-6-hydroxyphenyl) propionate, 1,2,2,6,6-pentamethyl-4-stearoyl piperidine, 2,2,6,6-tetramethyl-4-nitropiperidine, butylated reaction product of p-cresol and dicyclopentadiene, substituted amine oligomers, N,N'-bis(2,2,6,6-tetramethyl-4-piperidinyl)-1,6-hexanediamine, 2,4-dichloro-6-(4-morpholinyl)-1,3,5-triazine, N,N'-hexamethylene-bis[3-(3,5-di-t-butyl-4-hydroxyphenyl) propionamide], transition metals and compounds, mercapto compounds, phosphites, phosphonites hindered phenols and hindered amine antioxidants, polyketones and mixtures thereof.

22. A device as in claim 19 wherein the aromatic protectant polymer is an oxygen barrier polymer.

23. A catheter or balloon as in claim 13 wherein the radiation sensitive polymer is a member of the group consisting of aliphatic polyamides, aliphatic polyamide block copolymers, modified olefins, butyl rubbers, aliphatic polyesters, aliphatic polyurethanes and mixtures thereof.

24. A sterile medical catheter or balloon at least a portion of which is formed from thermoplastic polymer material wherein:
a) the thermoplastic polymer material comprises at least one radiation sensitive polymer which is an aliphatic polyester and at least one aromatic protectant polymer which is which is a member selected from the group consisting of polyphenylene oxides, aromatic polyurethanes, aromatic polyureas, aromatic polyamides, block copolymers of aromatic polyamides, and mixtures thereof, and
  i) the thermoplastic polymer material is a melt blend mixture comprising said radiation sensitive polymer and said aromatic protectant polymer, and/or
  ii) the thermoplastic polymer material comprises a multilayer laminate, at least one layer comprising said radiation sensitive polymer and at least one layer comprising said aromatic protectant polymer, and
b) the medical device has been sterilized with high energy radiation.

25. The catheter or balloon of claim 13 wherein the stabilizer is selected from the group consisting of 2-mercaptobenzimidazole, trilauryl phosphite, 2-mercaptobenzothiazole, N,N-di(β-napthyl-p-phenylenediamine, phenothiazine, 2,6-di-t-butylcresol, N-cyclohexyl-N'-phenyl-p-phenylenediamine, nickel dibutyldithiocarbamate, β-(3,5-di-t-butyl-6-hydroxyphenyl) propionate, 1,2,2,6,6-pentamethyl-4-stearoyl piperidine, 2,2,6,6-tetramethyl-4-nitropiperidine, butylated reaction product of p-cresol and dicyclopentadiene, substituted amine oligomers, N,N'-bis(2,2,6,6-tetramethyl-4-piperidinyl)-1,6-hexanediamine, 2,4-dichloro-6-(4-morpholinyl)-1,3,5-triazine, N,N'-hexamethylene-bis[3-(3,5-di-t-butyl-4-hydroxyphenyl)propionamide], transition metals and compounds, mercapto compounds, phosphites, phosphonites hindered phenols and hindered amine antioxidants, polyketones and mixtures thereof.

* * * * *

UNITED STATES PATENT AND TRADEMARK OFFICE
CERTIFICATE OF CORRECTION

PATENT NO. : 8,337,968 B2
APPLICATION NO. : 10/241278
DATED : December 25, 2012
INVENTOR(S) : Lixiao Wang et al.

It is certified that error appears in the above-identified patent and that said Letters Patent is hereby corrected as shown below:

In the Specifications:

Column 8, Line 15-20,

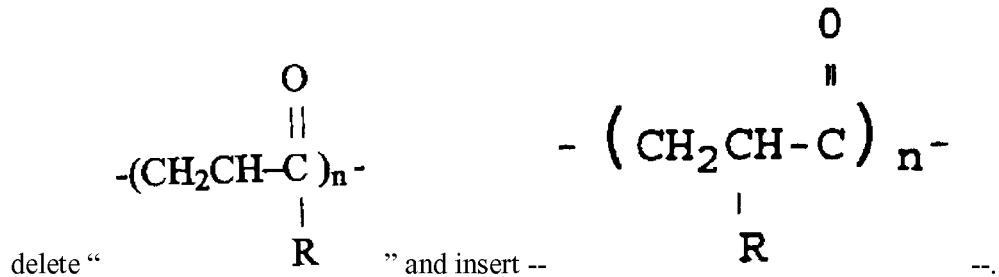

delete " " and insert -- --.

In the Claims:

Column 10, Claim 17, Line 50-55,

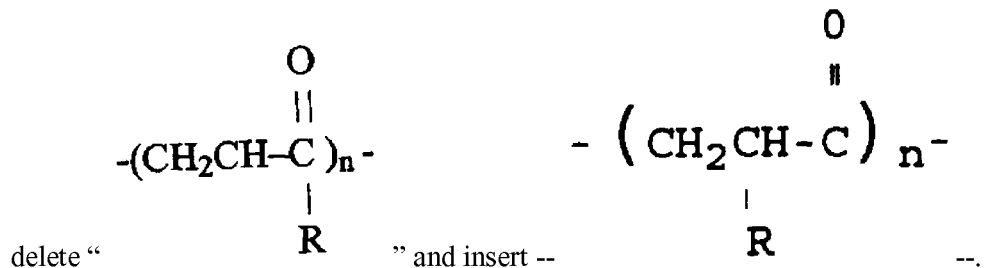

delete " " and insert -- --.

Signed and Sealed this
Sixth Day of August, 2013

Teresa Stanek Rea
*Acting Director of the United States Patent and Trademark Office*